United States Patent
Klingenstein

[11] Patent Number: 6,096,057
[45] Date of Patent: Aug. 1, 2000

[54] FECAL INCONTINENCE DEVICE AND METHOD

[76] Inventor: R. James Klingenstein, 151 Tremont St., Apt. 23E, Boston, Mass. 02111

[21] Appl. No.: 08/791,282

[22] Filed: Jan. 30, 1997

[51] Int. Cl.[7] .................................................. A61M 29/00
[52] U.S. Cl. ............................................... 606/197; 128/4
[58] Field of Search .............................. 128/4, 242, 246; 606/197, 192, 193

[56] References Cited

U.S. PATENT DOCUMENTS 3,882,852  5/1975  Sinnreich ..................................... 128/4
5,545,176  8/1996  Murtfeldt ................................. 606/192

Primary Examiner—Michael Buiz
Assistant Examiner—Anthony S. King
Attorney, Agent, or Firm—Testa, Hurwitz & Thibeault, LLP

[57] ABSTRACT

Provided is a device to control fecal incontinence and methods for its use. The device comprises a longitudinal tubular member having attached thereto bilaterally-extending wings for securing the device while in use. The device also comprises an expandable portion for prevention of unwanted defecation during use of the device.

23 Claims, 3 Drawing Sheets

FECAL INCONTINENCE DEVICE AND METHOD

FIELD OF THE INVENTION

The invention relates to rectal continence devices and methods which permit comfortable sitting, standing, and walking. Devices and methods of the invention are useful for treating fecal incontinence.

BACKGROUND OF THE INVENTION

Fecal incontinence typically is a source of physical discomfort and the cause of social and personal debilitation. It is most likely to affect the aged or individuals suffering from neurological trauma. However, abnormalities in stool volume or consistency, colonic transit, anal sphincter function, anorectal sensation, or anorectal reflexes also may result in incontinence. Madoff, et al., *New. Eng. J. Med.*, 326:1002–1007 (1992). Finally, a significant number of incontinence cases involve postpartum pelvic neuropathies, and thus may affect women at a relatively young age.

Mild cases of fecal incontinence typically are treated by instituting dietary changes. Biofeedback therapies also have been proposed in which a balloon, inserted in the rectum, provides a sensation similar to that of stool immediately prior to voiding. The patient is trained to perceive differing volumes of distention in the balloon and to respond accordingly by contracting and relaxing the anal sphincter muscles. See, e.g., Cerulli, et al., *Gastroenterology*, 76: 742–746 (1979).

Surgical remedies for severe cases of fecal incontinence include sphincter repair, placation of the posterior sphincter, anal encirclement in which a metal or elastic band mechanically tightens the anus, and muscle transfer procedures. Each of these techniques attempts to create a passive barrier to stool. However, they typically produce poor results, including leakage of stool, infection, and fecal impaction.

Recently, it has been proposed that fecal incontinence that cannot be corrected by surgery or by other approaches may be treated by insertion into the rectum of an artificial anal sphincter consisting of an inflatable cuff. Christiansen, et al., *Dis. Colon Rectum*, 32: 432–436 (1989). The cuff may be manually controlled in order to regulate passage of stool. Still other devices for control of fecal incontinence have been proposed. For example, U.S. Pat. No. 4,850,986 reports a fecal incontinence device that includes a tube inserted in the rectum and held by an adhesive or a clip to the thigh. Fecal incontinence bags have also been reported as a means of collecting voided stool. Such bags generally include a portion that is inserted in the rectum and connected to a disposable collection bag. See, e.g., U.S. Pat. No. 4,917,692.

A problem with such non-surgical devices for controlling fecal incontinence is that they are intrusive and often make walking, sitting, and other activities difficult. Moreover, such devices are not easily controlled in order to allow voiding of stool when desired by the patient. Accordingly, there is a need in the art for means for controlling fecal incontinence that is convenient, relatively non-intrusive on daily physical activity, and easy to regulate and manipulate during use. Such means are provided by the present invention.

SUMMARY OF THE INVENTION

The present invention provides a device for controlling fecal incontinence and methods for its use. Generally, a device according to the invention comprises an expandable tubular member for insertion into the rectum of a patient. The tubular member has attached thereto a pair of bilaterally-extending wings, which may be detachable, that conform to the surface of the buttocks of a patient, thereby to maintain the position of the device in the rectum. It is preferred that the wings are flexibly attached to the tubular member in order to adapt to the size of the patient's buttocks. A use of the device comprises inserting the device into the rectum of a patient and expanding the diameter of the tubular member, or preferably a portion thereof, by, for example, forcing gas or liquid through the tubular member or a portion thereof. The device preferably is inserted such that the expanding portion is in the rectum, and not in the anal canal. For purposes of the invention, the term "tubular" means a generally cylindrical shape that may be comfortably inserted in the rectum of a patient. As such oblong, rectangular, or other shapes with rounded edges are contemplated.

In a preferred embodiment, a device according to the invention comprises an expandable or inflatable sheath (an inflatable sheath is one type of expandable sheath, and the two terms will be used interchangeably herein) defining a fully-enclosed space surrounding a portion of the tubular member, the portion having at least one opening that connects the hollow portion of the tubular member to the space defined by the sheath. Accordingly, when a gas or a fluid is forced through the tubular member, the sheath expands in accordance with the volume of gas or fluid as the gas or fluid enters the space defined by the sheath via the opening. A valve preferably is fixed at the distal (anal) end of the device, such that it is accessible, but not intrusive against sitting, standing, or walking. The valve is, therefore, preferably recessed such that its opening is flush with the anal opening.

Also in a preferred embodiment, a device of the invention comprises a hollow tubular member comprising a closed end and an open end, and further comprising a sheath that defines an enclosed space surrounding at least a portion of the tubular member; wherein the tubular member contains at least one opening that communicates between the hollow portion defined by the tubular member and the enclosed space created by the sheath. A preferred device further comprises a valve connected to the open (distal) end of the tubular member. The valve is capable of receiving means for inflating the sheath as, for example, a syringe, a pump or other device for forcing gas or liquid through the hollow portion of the tubular member. If the hollow tubular member is itself inflatable or expandable, the valve is attached to the open end of the tubular member and is capable of receiving means for directly inflating the tubular member.

Also in a preferred embodiment, a device according to the invention comprises a locking valve for prevention of backflow of material introduced to inflate the tubular member or the sheath and for releasing such material when desired in order to remove the device from the patient. In a preferred embodiment, a pump is removably attached to the valve.

In a preferred embodiment, a device according to the invention comprises a tubular member as defined above, and further comprises a hollow inner core, which may be a second tubular member disposed within the first tubular member, for expulsion of gas or fecal material without removal of the device. Such a device preferably comprises a receptacle attached to a distal end thereof for collecting gas or fecal material voided via the hollow inner core. Also in a preferred embodiment, the hollow inner core comprises a backflow valve, the opening of which can be controlled for expulsion of gas or fecal material during use of the device. Such a device may further comprise a filter at its proximal end in order to allow passage of only gas through the hollow inner core.

Also in a preferred embodiment, a device according to the invention comprises a first, hollow tubular member having an opening at both distal and proximal ends. For purposes of the invention, the distal end of the device refers to the end terminating at or near the anus when the device is in use. The proximal end is the end terminating in the rectum when the device is in use. The device further comprises a second, hollow tubular member which contains a sheath or balloon at its proximal end, and terminates in an inflation valve at its distal end. The second tubular member is inserted in the hollow space defined by the first tubular member, such that the terminal sheath extends through the proximal-end opening of the first tubular member. An optional introducer may be used to insert in a patient the first tubular member. The sheath is inflated by forcing gas or liquid through the second tubular member.

Also in a preferred embodiment, the first hollow tubular member comprises within it a venting shaft for release of gas or other material. The core shaft functions as the first tubular member described in the various embodiments disclosed herein.

A preferred device according to the invention is comprised of a biocompatible material, preferably plastic, latex, polyurethane, rubber, a polystyrene polymer or copolymer, or any combination of the above. In any case, the device is sufficiently flexible so as not to impede sitting, standing, or walking. For example, the tubular member may be collapsible to aid in sitting, such that an uninflated portion of the member collapses upon sitting. Alternatively, walls of the tubular member may be sufficiently thin so as to not be intrusive.

Numerous additional features and advantages of the invention will become apparent upon consideration of the following detailed description thereof.

DETAILED DESCRIPTION OF THE INVENTION

The present invention provides a device for controlling fecal incontinence. The device is preferably constructed of a soft, flexible, biocompatible material, such as plastic, rubber, or a synthetic compound, such as a styrene-butadiene copolymer. The size of the device may be varied to fit an individual patient, but a device of between about 1 inch and about 10 inches in length and about 0.25 to about 2.0 inches in diameter is sufficient for use in most patients. Patients with pathologically-lax rectums may have loose sphincters, and the size of the device may be adjusted to fit such patients. Physicians are capable of making such adjustments or they may order custom-fitting devices. Similarly, the size of the inflated sheath is adjusted for the individual patient, such that proper occlusion occurs, and a defecation reflex is not triggered.

A device of the invention provides an impedance in the rectum to unwanted defecation, while providing maximum comfort and flexibility for walking and sitting. Increased wearing comfort is achieved through the use of a soft, biocompatible material for insertion into the patient's rectum and bilateral wings in order to prevent slippage once the device is inserted. Preferably, a portion of the device comprising a first tubular member in the rectum is inflated, while the rest of the device (i.e., portions in the anal canal and posterior rectum) remains uninflated. However, it is also possible for the entire device to be inflated in order to form a plug. A valve for introduction of gas or liquid for inflation of the device, or portion thereof, is preferably situated near the anal opening so as to provide access for inflation. However, the valve is as unobtrusive as possible to sitting, standing, or walking (i.e., it does not protrude unnecessarily from the anus). In a preferred embodiment, the device comprises an attached balloon or sheath at its proximal end. The sheath is attached, as described below, to an outer surface of the tubular member with apertures communicating from an inner hollow chamber defined by the tubular member to an enclosed space defined by the sheath. The sheath is inflated by forcing gas or liquid through the device, wherein gas or liquid inflates the sheath by passing through the apertures. By using a locking valve, the device may be maintained in an inflated state until the patient desires to remove the device, at which time the sheath is deflated. A device of the invention may optionally contain a separate hollow core, or second tubular member, for expulsion of gas or other material during use of the device. For example, the second tubular member may be contained within the first tubular member and may extend beyond the first tubular member, terminating, for example, in an ostomy-type bag or other receptacle.

Figure 1A:
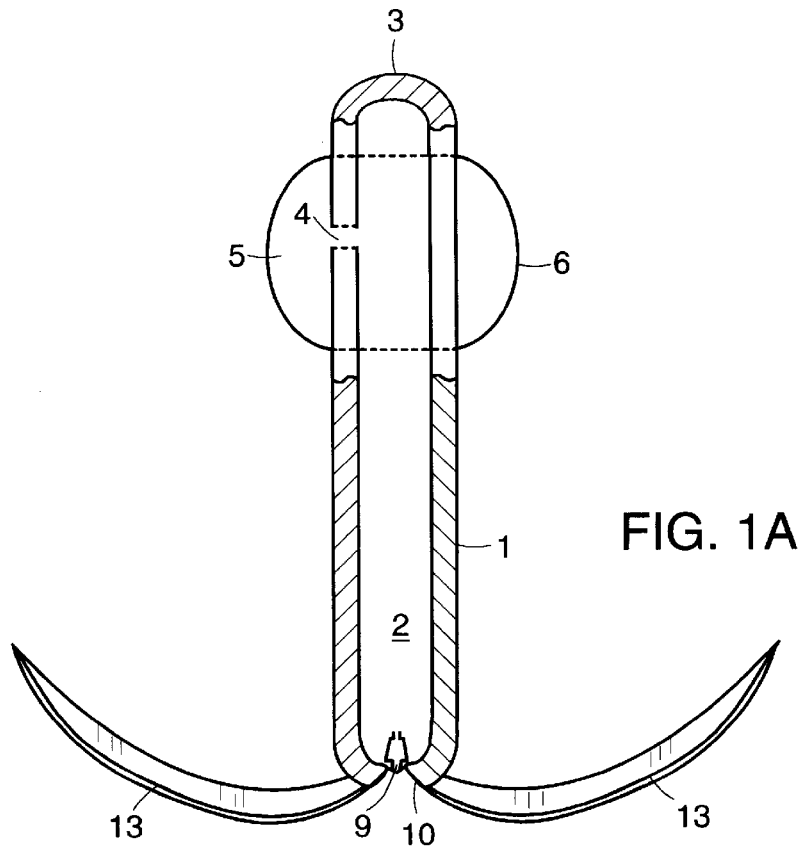
FIG. 1A is a sagittal section through a device according to the invention. The device is generally cylindrical with tapers at both ends. The Figure shows an inflated sheath 6, as would be the case when the device has been inserted for use. Broken shading in the Figure is for convenience in showing the region enveloped by the sheath.

A preferred device is shown in FIG. 1; wherein a hollow, tubular member 1 defines a longitudinal cavity 2 that terminates in a closed proximal end 3, which is preferably a rounded end for easy insertion in a patient. Near the closed proximal end 3, an opening 4 allows communication between the longitudinal cavity 2 and an enclosed space 5 created by an expandable sheath 6 that is disposed completely around the circumference of a portion of the tubular member 1 near the closed Proximal end 3 of the tubular member. The sheath 6 is constructed of a flexible material capable of being inflated. A valve 9 is installed at the open distal end 10 of the tubular member, the valve being capable of receiving a removable means (not shown) for expanding the sheath 6. Such means may be a syringe, a pump, or other pumping means which forces a gas, for example air, or a liquid, for example saline, through the longitudinal cavity 2 of the tubular member and further through the opening 4 into the interior space 5 so as to expand the sheath 6 to create a balloon (i.e., an inflated sheath). The valve 9 is preferably a locking valve, such as a Bardex® 5 cc Luer Lock valve.

Accordingly, upon introduction of gas or liquid into the cavity 2, the valve locks, causing the sheath to remain expanded until the valve is released. The expanded sheath, along with bilateral wings, aids in securing the device in the rectum.

Also at or near the open (distal) end 10 of the tubular member are bilateral wing structures 13 which aid in supporting the device when installed. The wings are preferably made of a soft biocompatible material and are flexible so as to conform to the buttocks and/or thighs of the patient in whom the device is installed. The wings cause the device to remain in place so as to maintain a proper seal between the ballooned sheath and the wall of the internal anal canal, thus preventing unwanted voiding of stool. The wings prevent the device from being inserted too far into the rectum and also prevent slippage which may cause the device to accidentally exit the rectum. An adhesive may be attached to an inner surface of the wings in order to aid attachment of the wings to the buttocks of the patient. The wings should be flexibly attached to the tubular member in order not to impede sitting, standing, or walking. The wings may wrap around the buttocks to the extent desired by the patient.

Use of the device comprises inserting the closed end portion of the tubular member into the rectum so that the distal end of the sheath securely abuts the internal wall of the anal canal. The device may be pre-lubricated, or a lubricant may be applied prior to insertion in order to aid in the insertion of the device. The valve should extend to at least the anal opening in order to allow insertion of the expanding means (e.g., a syringe) into the valve for inflation of the sheath. Once the device is secured in the rectum, the syringe or other appropriate expanding means is used to expand the sheath. The sheath is expanded so as to prevent passage of stool through the anal opening, but must not be expanded to such an extent as to trigger a defecation reflex. Ideally, the patient should not feel the expanded sheath. Once the sheath is expanded, the pumping means is removed and the wings are secured in place along the buttocks. When the patient desires to defecate, the device is removed by allowing air or gas to escape the ballooned portion of the tubular member by, for example, reinsertion of the pumping means, causing the sheath or inflated portion of the first tubular member to deflate, which enables easy removal of the device.

Figure 3:
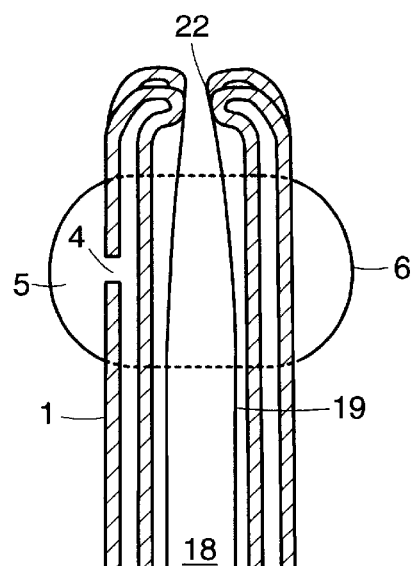
FIG. 3 is a sagittal section through a device of the invention. The device comprises an inflatable sheath that is inflated by introduction of gas or fluid via a hollow portion of the outer wall of a first tubular member; and a second tubular member disposed within a hollow space created by the first tubular member for release of gas and/or fecal material while the device is in use.
Figure 3:
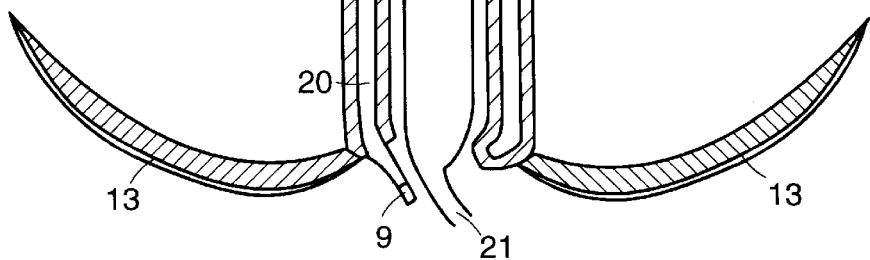

In an alternative embodiment, shown in FIG. 3, a device according to the invention comprises a first, outer hollow tubular member 1 and a second, inner hollow tubular member 19 defining a core 18, the second member being disposed within the first member. The first, hollow tubular member 1 comprises a hollow outer core 20 for inflation of the sheath 6. As shown in FIG. 3, a valve 9 is attached to the distal terminal of the outer core 20. In order to inflate the sheath 6, an inflation means is attached to the valve as described above. Also as described above, the valve is accessible, but not intrusive to daily physical activity, as, for example, walking or sitting. Gas or liquid pumped through the outer core 20 inflates the sheath 6 by passing through appeture 4. The second inner hollow tubular member 19 defines an enclosed central shaft or core 18. The shaft or core 18 communicates between openings at both proximal and distal ends of the device in order to allow regulated expulsion of gas and/or fecal material through an exit tube 21 without removing the device. The exit tube 21 extends out of the anus and communicates with a collection apparatus, preferably an ostomy bag. As shown in the figure, the proximal portion of the second member terminates in an opening to the rectum. The proximal portion of the second member may attach to the proximal portion of the first member, as shown, or may be inserted independently through the hollow portion of the first member. While the figures are sagittal sections through alternative devices of the invention, it is understood that a device of the invention takes on a generally cylindrical shape, thus forming a tube, or series of tubes. In addition, a filter may be placed at the proximal end 22 of the shaft in order to allow passage only of gas and not fecal matter. Use of this embodiment increases wearing time and the physical comfort of the patient.

Figure 1B:
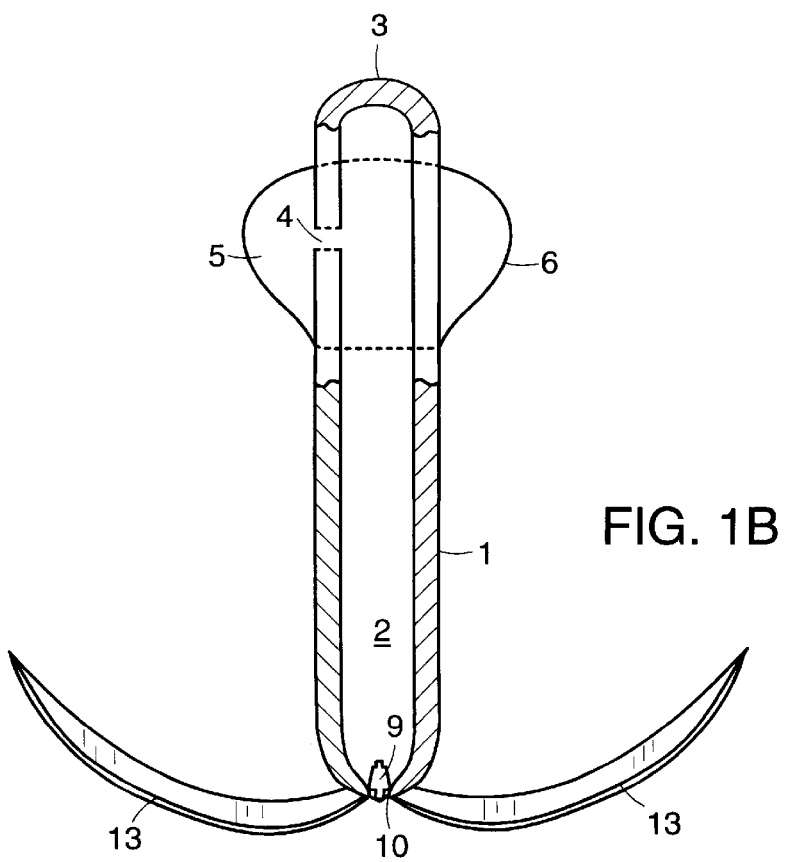
FIG. 1B is a sagittal section through a device according to the invention showing a tapered sheath or balloon.
Figure 2:
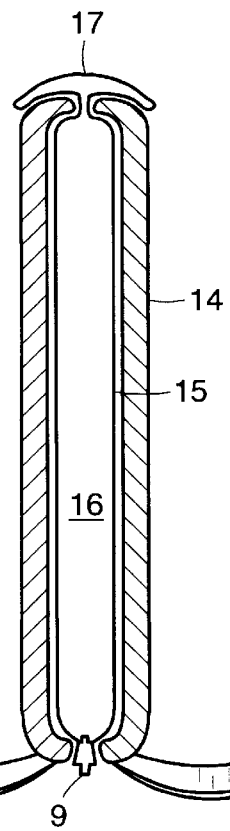
FIG. 2 is a sagittal section through a device of the invention in which a first, hollow tubular member is inserted in a patient's rectum, and a second, hollow tubular member is inserted through the hollow space of the first tubular member. The second tubular member terminates at its proximal end in an inflatable sheath (e.g., a balloon), shown uninflated in the figure.
Figure 2:
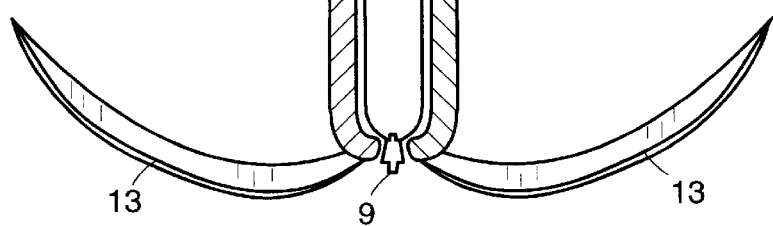

As shown in FIG. 2, a further embodiment of the invention comprises a first hollow tubular member comprising two open ends (proximal and distal on the tube), and a second hollow tubular member 15, defining a hollow space 16. The proximal end of the second member 15 terminates in a sheath or balloon 17 (shown uninflated), which may be fixedly attached or may be removably attached to promote reuse of the second member. A valve 9 is attached to the distal end of the second member, protruding past the distal opening of the first member and being accessible to an inflation means. Introduction of gas or fluid via the valve 9 causes the sheath 17 to be inflated, thus providing an occlusion of the rectum. When inflated, it is preferred that the sheath is tapered at its distal end in order to secure the inflated sheath against the internal anal sphincter, and so that the sheath conforms to the shape of the distal rectum. Tapering is possible in any embodiment of the invention by, for example, varying the thickness and/or elasticity of the walls of the sheath. FIG. 1B shows a tapered sheath 6 according to one embodiment of the invention.

Flexible wings are attached to the first member in order to provide increased comfort and stability of the device during use. In this embodiment, the first member may be inserted independently of the second member, providing a channel for later insertion of the second member with attached sheath. Alternatively, the device may be inserted as a unit. Use of this device provides increased wearing time, and renders the device re-usable.

Figure 4:
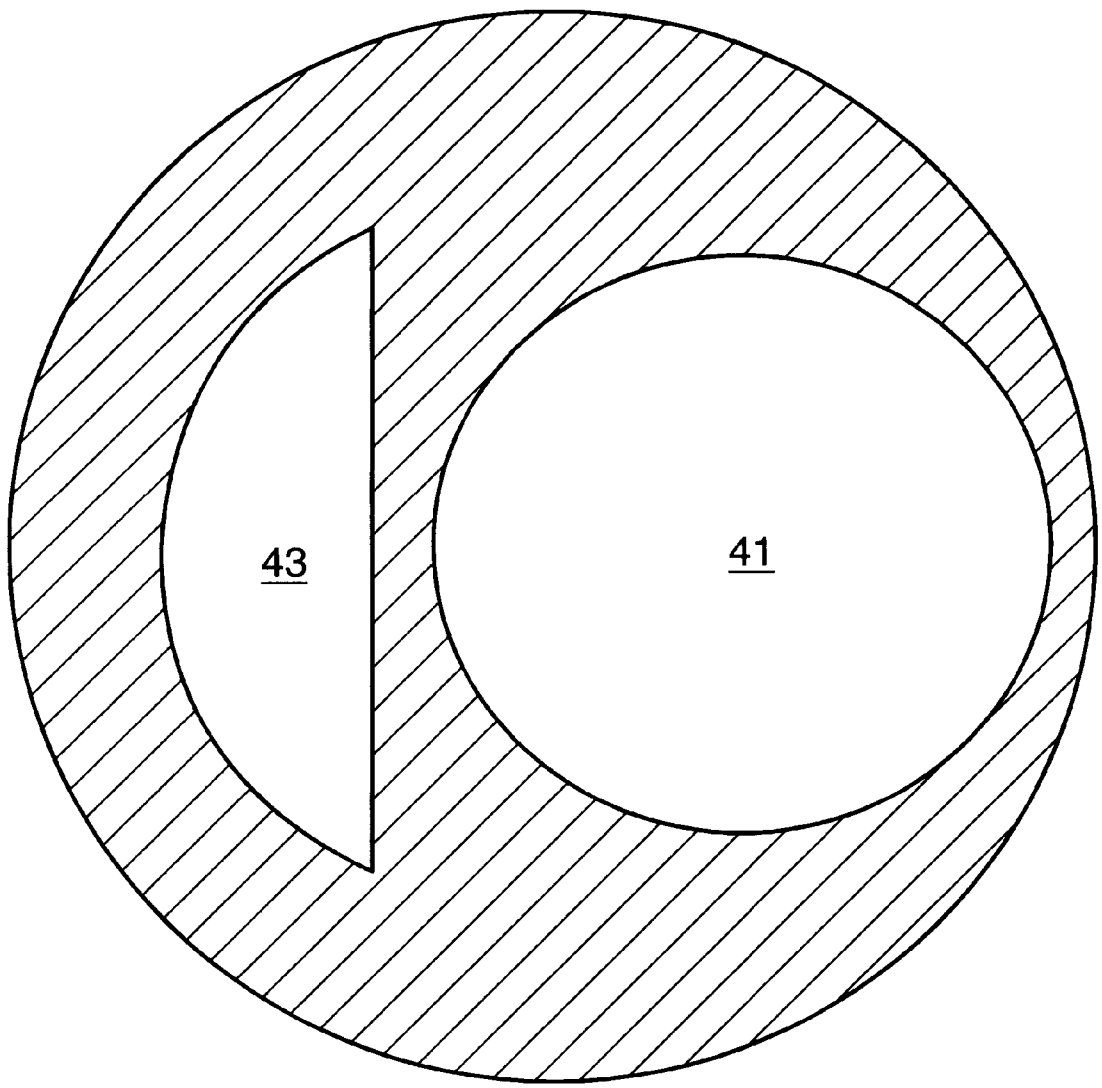
FIG. 4 is a cross-section of a first tubular member comprising both a central hollow shaft for inflation of a sheath or balloon, or for introduction of an rod or core bearing a sheath; and a venting shaft for release of gas and/or waste material.

In a further alternative embodiment, the first, hollow tubular member may house both a central shaft for inflation of a sheath or balloon, and a venting shaft for controlled release of gas while the device is in use. FIG. 4 is a cross-section of a first hollow tubular member that houses a core shaft 41 for inflation of a sheath, and a venting shaft 43 for controlled release of gas and/or waste material. The total diameter of the combined shafts is no greater than that of the core shaft shown in FIGS. 1A and 1B. Preferably, the shaft linings are constructed of a flexible material that accommodates increased pressure (and the resultant increase in diameter) caused by either inflation of the sheath or expulsion of gas, or both.

The core shaft 41 of FIG. 4 may terminate in a valve for inflation as described above, or may be an open-ended conduit for an insert containing an inflation means as described above, and as shown in FIG. 3. The venting shaft shown in FIG. 4 need not be of any particular shape, and may span the circumference of the tubular member, forming a hollow tube that completely surrounds the core shaft 41. As shown in FIG. 4, the venting shaft 43 is uninflated. The venting shaft 43, is sufficiently flexible to expand when gas or other material passes through the vent.

Other features of the device will become apparent upon consideration of the foregoing description. Accordingly, the invention is limited only by the scope of the appended claims.

What is claimed is:

1. A device for controlling fecal incontinence, comprising:

a tubular member; and bilaterally-extending wings attached to an end of said tubular member said wings capable of being shaped to conform to the contour of a patient's buttocks;

wherein at least a portion of the tubular member is expandable.

2. The device of claim 1, further comprising means for expanding said sheath.

3. The device of claim 1; wherein said tubular member comprises material selected from the group consisting of plastic, rubber, and polyurethane.

4. A device for preventing unwanted expulsion of fecal material, comprising:

a hollow, tubular member defining a single longitudinal cavity that terminates at a closed proximal end of said tubular member; and an expandable sheath that defines an enclosed space surrounding a portion of said tubular member; wherein said portion comprises at least one opening communicating between said enclosed space and said longitudinal cavity defined by said hollow, tubular member; and bilateral wings attached to said tubular member said wings shaped to conform to the contour of a patient's buttocks.

5. The device of claim 4 further comprising an open end to said rigid, hollow tubular member, and a valve connected to said open end, said valve being capable of receiving a pump for inflating said sheath.

6. The device of claim 5, wherein said pump is a syringe.

7. The device of claim 5 wherein said valve is a locking valve for prevention of backflow of material introduced into said hollow tubular member.

8. The device of claim 5, wherein said sheath is tapered to conform to the shape of the patient's distal rectum.

9. A device for controlling fecal incontinence, comprising:

a first tubular member defining a hollow space, and having two open ends;

a second tubular member disposed within said first tubular member, and having two open ends;

and an expandable sheath defining an enclosed space surrounding a portion of said first tubular member; and at least one opening communicating between said hollow space and a cavity defined by said sheath.

10. The device of claim 9 further comprising a valve attached to said first tubular member for inflation of said sheath.

11. The device of claim 10 further comprising bilaterally-extending wings attached to said first member.

12. The device of claim 11 wherein said bilaterally extending wings are flexibly attached.

13. The device of claim 12, wherein said wings are detachable.

14. The device of claim 9, wherein said first tubular member further comprises a filter.

15. A device for controlling fecal incontinence, comprising:

a first hollow tubular member comprising two open ends;

a second hollow tubular member disposed within an internal hollow space created by said first hollow tubular member;

a valve fixedly attached to said second hollow tubular member; and an expandable sheath attached to an end of said second hollow tubular member.

16. The device of claim 15 further comprising bilaterally-extending wings attached to said first member.

17. The device of claim 16 wherein said bilaterally-extending wings are flexibly attached.

18. The device of claim 1 or 17, wherein said bilaterally-extending wings are flexibly-attached to said tubular member.

19. The device of claim 11 or 16, wherein said bilaterally-extending wings comprise an adhesive for attachment to a patient's buttocks.

20. The device of claim 15, further comprising means for inflating said sheath.

21. The device of claim 15, wherein said valve is a locking valve for prevention of backflow of material introduced into said second hollow tubular member.

22. The device of claim 17, wherein said first hollow tubular member is removably attached to a receptacle.

23. The device of claim 15, wherein said valve is recessed within said second hollow tubular member.

* * * * *

UNITED STATES PATENT AND TRADEMARK OFFICE
CERTIFICATE OF CORRECTION

PATENT NO. : 6,096,057                                                     Page 1 of 2

DATED : August 1, 2000

INVENTOR(S) : Klingenstein

It is certified that error appears in the above-identified patent and that said Letters Patent is hereby corrected as shown below:

In claim 22, column 8, line 41, "17" should be deleted and replaced with --15--.

Under "References Cited - U.S. PATENT DOCUMENTS" on the cover page, the following reference should be inserted before the line referring to "3,882,852":

--1,282,881    12/1918    Landis--

Under "References Cited - U.S. PATENT DOCUMENTS" on the cover page, the following reference should be inserted after the line referring to "3,882,852":

--4,686,985    8/1997    Lottick--

Under "References Cited - U.S. PATENT DOCUMENTS" on the cover page, the following reference should be inserted after the line referring to "5,545,176":

--5,603,685    2/1997    Tutrone, Jr.
5,702,421    12/1997    Schneidt--

Under "References Cited" on the cover page, the following should be inserted:

--FOREIGN DOCUMENTS

68318EP    5/1983    Europe--.

UNITED STATES PATENT AND TRADEMARK OFFICE
CERTIFICATE OF CORRECTION

PATENT NO. : 6,096,057
DATED : August 1, 2000
INVENTOR(S) : Klingenstein

It is certified that error appears in the above-identified patent and that said Letters Patent is hereby corrected as shown below:

Under "References Cited" on the cover page, the following should be inserted:

-- OTHER PUBLICATIONS

Cerulli et al. (1979) "Progress in biofeedback conditioning for fecal incontinence," Gastroenterology 76:742-746
Christiansen et al., (1989) "Implantation of artificial sphincter for anal incontinence. Report of five cases," Dis Colon Rectum 32:432-436
Madoff et al., (1992) "Fecal incontinence," N. Engl. J. Med. 326:1002-1007--

Signed and Sealed this

Twenty-fourth Day of April, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO.   : 6,096,057
DATED        : August 1, 2000
INVENTOR(S)  : Klingenstein It is certified that error appears in the above-identified patent and that said Letters Patent is hereby corrected as shown below:

Column 7,
Line 37, "5" should be deleted and replaced with -- 4 --.

Signed and Sealed this

Ninth Day of September, 2003

JAMES E. ROGAN
*Director of the United States Patent and Trademark Office*